United States Patent [19]

Witzeman et al.

[11] Patent Number: 5,113,011

[45] Date of Patent: *May 12, 1992

[54] METHOD OF FUNCTIONALIZATION OF NUCLEOPHILES

[75] Inventors: J. Stewart Witzeman; W. Dell Nottingham, both of Kingsport, Tenn.

[73] Assignee: Eastman Kodak Company, Rochester, N.Y.

[*] Notice: The portion of the term of this patent subsequent to Sep. 24, 2008 has been disclaimed.

[21] Appl. No.: 735,082

[22] Filed: Jul. 24, 1991

Related U.S. Application Data

[63] Continuation of Ser. No. 620,388, Nov. 30, 1990, Pat. No. 5,051,529, which is a continuation of Ser. No. 484,595, Feb. 26, 1990, abandoned, which is a continuation-in-part of Ser. No. 283,353, Dec. 12, 1988, abandoned.

[51] Int. Cl.$^5$ ................................................ C08F 8/00
[52] U.S. Cl. ................................. 560/178; 505/328.8; 505/383; 505/386; 505/437
[58] Field of Search ............... 560/178; 525/383, 386, 525/437

[56] References Cited

U.S. PATENT DOCUMENTS

| | | | |
|---|---|---|---|
| 3,988,476 | 10/1976 | Buckle et al. | 514/677 |
| 4,134,894 | 1/1979 | Zinnes et al. | 548/428 |
| 4,175,203 | 11/1979 | Cragoe, Jr. et al. | 560/55 |
| 4,332,965 | 6/1982 | Dalibor | 560/169 |
| 4,402,969 | 9/1983 | Greenlee et al. | 548/496 |
| 4,427,586 | 1/1984 | Numata et al. | 540/200 |

FOREIGN PATENT DOCUMENTS 227454 7/1987 European Pat. Off. .

OTHER PUBLICATIONS

Gilbert and Kelly, Journal of Organic Chemistry, vol. 53, pp. 449–450 (1988).
Carroll, Proceedings of XIth International Congress of Pure and Applied Chemistry, vol. 39, p. 2 (1947); as cited in Chem Abstracts, vol. 45, col. 7015 (1951).
Seebach et al, Synthesis, 1982, pp. 138–141.
Bader et al, Journal of the American Chemical Society, vol. 73, pp., 4195–4197 (1951).
Bader and Vogel, Journal of the American Chemical Society, vol. 74, pp. 3992–3994 (1952).
Taber et al, Journal of Organic Chemistry, vol. 50, pp. 3618–3619 (1985).

Primary Examiner—Bernard Lipman
Attorney, Agent, or Firm—Oblon, Spivak, McClelland, Maier & Neustadt

[57] ABSTRACT

Process for the preparation of acetoacetates and other $\beta$-ketoesters is provided, involving reaction of nitrogen, oxygen or sulfur nucleophiles with a tertiaryalkyl acetoacetate or tertiaryalkyl-$\beta$-ketoester.

2 Claims, No Drawings

METHOD OF FUNCTIONALIZATION OF NUCLEOPHILES

This application is a continuation of my copending application Ser. No. 07/620,388, filed Nov. 30, 1990, now U.S. Pat. No. 5,051,529 which was a continuation of my application Ser. No. 07/484,595, filed Feb. 26, 1990, now abandoned, which was a continuation-in-part of my copending application Ser. No. 07/283,353, filed Dec. 12, 1988, now abandoned.

This invention relates to the functionalization of nucleophiles with $\beta$-dicarbonyl compounds. In one aspect, this invention relates to the acetoacetylation of nucleophiles. In another aspect, this invention relates to the acetoacetylation of low molecular weight nucleophiles. In yet another aspect, this invention relates to the acetoacetylation of polymeric nucleophiles.

BACKGROUND

The acetoacetate moiety has been used in the coatings industry to impart functionality capable of undergoing a variety of cross-linking reaction while simultaneously lowering the viscosity of the resulting formulation. Among the reactions which can be used to promote cross-linking of acetoacetylated polymeric materials are reactions with activated olefins (commonly referred to as the Michael reaction), diamines, melamine, isocyanates, and the like. Coatings prepared from acetoacetylated polymers using such cross-linking strategies often exhibit improved stain-resistance, salt-spray resistance and better adhesion to the metal surface when compared to coatings prepared from nonacetoacetylated polymers.

Interest in the use of acetoacetylated materials in coatings has led to the need for general synthetic procedures for the preparation of acetoacetylated compounds which can be readily practiced on industrial scale. It is known that acetoacetylated acrylic resins can be prepared by the copolymerization of acetoacetoxyethyl methacrylate with acrylic or methacrylic monomers. Alternatively, acetoacetylated polymers or resins can be prepared by the acetoacetylation of the polymeric substrate, rather than by polymerization of acetoacetylated monomers. One substrate for which this method of synthesis is generally required is in the preparation of acetoacetylated polyester resins.

Simple acetoacetylated materials can be prepared in a variety of ways. For example, an appropriate nucleophile can be treated with diketene. Alternatively, such nucleophile can be subjected to a thermal reaction with 2,2,6-trimethyl-4H-1,3-dioxin-4.one (TKD, the diketene-acetone adduct). As yet another alternative, such nucleophile can be subjected to transesterification with another acetoacetate moiety (referred to hereinafter as "transacetoacetylation").

The industrial-scale use of diketene for such applications is impractical due to strict governmental regulations regarding the shipping of this material. In addition, the classification of diketene as a lachrymator make the large scale use of this material undesirable. The dioxinone, TKD, while effective for acetoacetylation, is currently too costly a raw material to be employed for large scale industrial applications.

While transesterification reactions are well known in the preparation of polyester coating resins, transesterification of acetoacetates (i.e., transacetoacetylation) has not found wide spread application. One published procedure for the preparation of acetoacetic acid derivatives involves heating solutions of a higher boiling alcohol with an excess of methyl or ethyl acetoacetate while the volatile methyl or ethyl alcohol co-product is removed by distillation. Reaction times for such procedure are on the order of many hours when carried out at elevated temperatures (about 100° C). Another method for transacetoacetylation which has been suggested in the art involves contacting the alcohol of interest with a large excess of methylacetoacetate and a 4-dimethylaminopyridine catalyst in a high boiling hydrocarbon solvent such as toluene for an extended period of time. An alternate method for transacetoacetylation disclosed in the art is the use of titanium catalysts.

Seebach et al, Synthesis, 1982, pages 138–141, disclose the use of substantial amounts of titanium (IV) alkoxides (tetraalkyl titanates) as catalysts in the transacetacetylation of alcohols. More specifically, this reference discloses the reaction of tertiary (t) butyl acetoacetate with n-butanol and benzyl alcohol in the presence of tetraethyl titanate wherein the molar ratio of the titanate used to t-butyl acetoacetate was 0.21 or 0.35.

Yet another prior art disclosure of transesterification reactions employing acetoacetic moieties is found in European Patent Application 227,454, assigned to Cook Paint and Varnish Inc. The reaction between a polyhydroxy functional monomer or polymer and an alkyl monofunctional acetoacetate is disclosed. Suitable acetoacetate esters are disclosed to be methyl acetoacetate, ethyl acetoacetate, isopropyl acetoacetate, butyl acetoacetate, t-butyl acetoacetate, methyl benzyl acetoacetate and dodecyl acetoacetate. The examples in this disclosure demonstrate only the use of ethyl acetoacetate. There is no suggestion in the reference of any benefit from using one acetoacetate moiety rather than another taken from the above list of "suitable" compounds.

The high dilution, large amounts of catalyst used and long reaction times involved make each of the prior procedures for transacetoacetylation impractical, especially when application on a commercial scale is contemplated. Prior art procedures are particularly ill-suited for the acetoacetylation of higher molecular weight (including polymeric) nucleophiles. There is, therefore, a need in the art for simplified procedure for transacetoacetylation, which procedure does not require extreme reaction conditions or large quantities of unreactive materials.

STATEMENT OF THE INVENTION

In accordance with the present invention, we have discovered that a variety of nucleophiles can be functionalized by contacting such nucleophiles with a specifically defined $\beta$-dicarbonyl compound, i.e., a $\beta$-ketoester as defined below under moderate reaction conditions of time and temperature.

The invention functionalization process is relatively rapid, can be carried out in the substantial absence of catalysts and/or solvent, avoids the use of toxic and/or more expensive starting materials, is of very general applicability, provides products with low level of residual color, and produces volatile and readily recoverable coproducts.

DETAILED DESCRIPTION OF THE INVENTION

In accordance with the present invention, there is provided a method for the functionalization of nucleophiles having the structural formula:

wherein Y is selected from nitrogen, oxygen or sulfur;

wherein R is selected from the group consisting of:

$C_1$ up to $C_{12}$ hydrocarbyl radical substituted with 0 up to 3 hydroxyl units, formyl units, nitro units, chlorine atoms, bromine atoms, ester moieties of the structure:

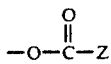

wherein Z is a hydrocarbyl moiety having in the range of 1 up to 6 carbon atoms, or alkoxy moieties of the structure, —OZ, wherein Z is as defined above; and wherein R can also be H when Y is N; and wherein x is 1 when Y is 0 or S, and x is 2 when Y is N;

said process comprising contacting said nucleophile with a β-ketoester compound having the structure;

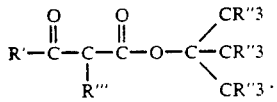

wherein

R' is a $C_1$ up to $C_8$ alkyl, aryl or halide substituted alkyl or aryl moiety, each R" is independently selected from H, a $C_1$ up to $C_8$ alkyl moiety, or a halogen, and R''' is selected from H, $C_1$ up to $C_4$ alkyl moieties, $C_4$ up to $C_{10}$ aromatic, heteroaromatic and substituted aromatic moieties, or halogens;

wherein said contacting is carried out in the essential absence of a tetraalkyl titanate and at a temperature and for a time sufficient to produce the desired product.

In accordance with an alternate embodiment of the present invention, there is provided a method for the functionalization of nucleophiles having the structural formula:

wherein Y is selected from nitrogen, oxygen or sulfur;

wherein R is selected from:

i) hydroxylated polyesters having a number average molecular weight in the range of about 500 up to 10,000, or ii) acrylic polymers containing free hydroxyl groups and having a number average molecular weight in the range of about 500 up to 10,000; and wherein R can also be H when Y is N; and wherein x is 1 when Y is 0 or S, and x is 2 wherein Y is N;

said process comprising contacting said nucleophile with a compound having the structure:

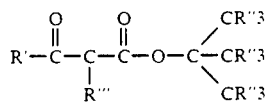

wherein

R' is a $C_1$ up to $C_8$ alkyl, aryl or halide substituted alkyl or aryl moiety, each R" is independently selected from H, a $C_1$ to $C_8$ alkyl moiety, or a halogen, and R''' is selected from H, $C_1$ up to $C_4$ alkyl moieties, $C_4$ up to $C_{10}$ aromatic, heteroaromatic and substituted aromatic moieties, or halogens;

wherein said contacting is carried out in the essential absence of a tetraalkyl titanate and at a temperature and for a time sufficient to produce the desired product.

Nucleophiles contemplated for the use in the practice of the present invention include, inter alia, alkanols, alkylamines, alkylthiols, aryl alcohols, aryl amines and arylthiols. Alkyl moieties having in the range of 1 up to 12 carbon atoms are contemplated, while aryl moieties having in the range of 4 up to 12 carbon atoms are contemplated. Exemplary nucleophiles of this type include n-butanol, octanol, butyl amine, dibutyl amine, aniline, phenol, thiophenol, benzyl alcohol, nitroaniline, 1-methyl-1-cyclohexanol, and the like.

Additional nucleophiles contemplated for use in the practice of the present invention include allyl alcohols having the structure:

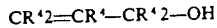

wherein each $R^4$ is independently selected from the group consisting of hydrogen and hydrocarbyl radicals having 1 up to 4 carbon atoms. Exemplary nucleophiles of this type include allyl alcohol, 3-methyl-2-buten-1-ol, 2-methyl-2-propen-1-ol, 3-methyl-3-buten-2-ol, and the like.

Acrylates having the structure:

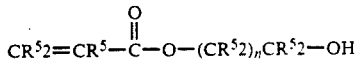

are also contemplated for use in the practice of the present invention. Each $R^5$ is independently selected from hydrogen, methyl or ethyl radicals, and n can vary from 1 up to 6. Exemplary acrylate moieties satisfying this structure include hydroxyethyl methacrylate, hydroxyethyl acrylate, hydroxybutyl methacrylate, hydroxybutyl acrylate, and the like.

Polyol nucleophiles contemplated for use in the practice of the present invention have the general structure:

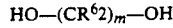

wherein each $R^6$ is independently selected from the group consisting of hydrogen, hydroxy, and alkylene radicals having 1 up to 4 carbon atoms, while m can vary from 2 up to about 12.

Polymeric nucleophiles contemplated for use in the practice of the present invention include i) hydroxylated polyesters having a number average molecular weight in the range of about 500 up to 10,000 or (ii) acrylic polymers containing free hydroxyl groups and having a number average molecular weight in the range of about 500 up to 10,000.

Preferred hydroxylated polyesters have the structure:

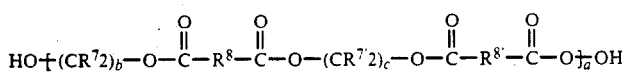

wherein each $R^7$ and $R^{7'}$ is independently selected from H, $C_1$ up to $C_4$ alkyl, hydroxy, or alkoxy of the structure, —OZ, wherein Z is a hydrocarbyl moiety having in the range of 1 up to 6 carbon atoms; and each $R^8$ and $R^{8'}$ is independently selected from 1,2-arylene, 1,3-arylene, 1,4-arylene or an alkylene moiety of the structure:

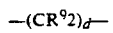

wherein each $R^9$ is independently selected from H, $C_1$ up to $C_4$ alkyl, hydroxy or alkoxy of the structure —OZ, wherein Z is a hydrocarbyl moiety having in the range of 1 up to 6 carbon atoms, and d is a whole number which can vary from 0 up to 24;

a can vary from 1 up to 20;

b can vary from 2 up to 12; and c can vary from 2 up to 12.

Exemplary materials which conform to this generic formula include hydroxylated polyesters having a number average molecular weight in the range of about 500 up to 6000 and comprising at least one dicarboxylic moiety selected from the group consisting of phthalic acid, terephthalic acid, isophthalic acid, adipic acid, 1,4-cyclohexanedicarboxylic acid, 1,3-cyclohexanedicarboxylic acid, 1,2-cyclohexanedicarboxylic acid, and esters thereof; and at least one polyol selected from the group consisting of ethylene glycol, propylene glycol, pentaerythritol, neopentylglycol, 2,2,4-trimethyl-1,3-pentanediol, glycerol, 1,1,1-trimethylolpropane, and 1,1,1-trimethylolethane.

Preferred acrylic polymers employed in the practice of the present invention are polymers prepared from hydroxyethyl methacrylate, hydroxyethyl acrylate, 4-hydroxybutyl acrylate and/or 4-hydroxybutyl methacrylate with at least one comonomer selected from the group consisting of methyl acrylate, ethyl acrylate, propyl acrylate, butyl acrylate, methyl methacrylate, ethyl methacrylate, propyl methacrylate, and butyl methacrylate.

β-Ketoester compounds contemplated for use in the practice of the present invention are compounds having the structure:

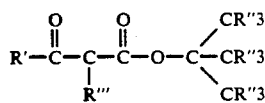

wherein

R' is a $C_1$ up to $C_8$ alkyl aryl or halide substituted alkyl or aryl moiety, each R" is independently selected from H, a $C_1$ up to $C_8$ alkyl moiety, or a halogen, and R''' is selected from H, $C_1$ up to $C_4$ alkyl moieties, $C_4$ up to $C_{10}$ aromatic, heteroaromatic and substituted aromatic moieties, or halogens.

Preferred β-ketoesters useful in the practice of the present invention include compounds wherein R' is methyl or tertiary butyl, R" is H or a $C_1$ up to $C_4$ alkyl moiety and R''' is H, a $C_1$ up to $C_4$ alkyl moiety or a chloride radical.

Presently most preferred β-ketoester moieties for use in the practice of the present invention include t-butyl acetoacetate, 2-chloro-t-butyl acetoacetate, t-butyl pivaloyl acetate, and t-amyl acetoacetate. Presently most preferred acetoacetates are t-butyl acetoacetate and t-butyl pivaloyl acetate, because of the ready availability and high reactivity of these compounds.

When t-butyl pivaloyl acetate is employed as the acetoacetylating moiety, a particularly preferred nucleophile to employ in the practice of the present invention is 2-chloro-4-nitroaniline. This combination of reagents gives much more rapid reaction to produce the desired product than does the reaction of 2-chloro-4-nitroaniline with methyl pivaloyl acetate.

The invention reaction can be carried out under a wide variety of conditions. For example, reaction can be carried out in the presence or absence of solvent. When employed, suitable solvents include aromatic hydrocarbons (e.g., toluene, xylene, and the like) esters, e.g., butyl acetate, ethyl amyl acetate, ethyl-3-ethoxy propionate, and the like), ketones (e.g., methyl isobutyl ketone, methyl amyl ketone, methyl isoamyl ketone, ethyl butyl ketone, and the like), as well as any of the above solvents used in conjunction with a material capable of azeotroping with t-butanol (e.g., cyclohexane).

When solvent is employed, concentrations of β-ketoester of from about 0.1 up to 10 moles per liter can be employed, depending on the solubility of the nucleophile to be employed.

The invention process can be carried out at a wide range of temperatures. Typical temperatures fall in the range of about 80° up to 200° C., with temperatures in the range of about 90° up to 160° C. being preferred.

Reaction times in the range of about 0.5 up to 24 hours are generally suitable. Preferably, reaction times in the range of about 0.5 up to 8 hours are employed. Those of skill in the art recognize that the desired reaction time will vary as a function of numerous variables, such as, for example, reaction temperature, the desired degree of conversion, the particular reactants employed, and so on.

As specified hereinabove, the process of the present invention is carried out in the essential absence of tetraalkyl titanate compounds such as those described by Seebach et al in the reference cited above, e.g., in the absence of tetraalkyl titantes in amounts in which they are typically used to catalyze transesterification reactions. Preferably, the process is performed in the absence of transesterification catalysts in general.

The invention will now be described in greater detail by reference to the following nonlimiting examples.

EXAMPLE 1

Several methods for functionalization of nucleophiles in accordance with the present invention are illustrated below.

Method A

The preparation of the bis-acetoacetate of neopentyl glycol (NPG) is illustrative of this procedure. In a 125 mL Erlenmeyer flask with magnetic stirrer and thermometer was placed 10.03 g NPG (0.096 mole), 32.1 g tertiary butyl acetoacetate (tBAA; 0.203 mol) and 32 mL xylene. The solution was heated with stirring on a hot plate to the boiling point of xylene. Once the solution reached 138° C. (ca. 10 min) the solution was removed from the hot plate, cooled to room temperature, concentrated in vacuo and short-path distilled to yield 22.83 g (87.1%) bis-acetoacetate b.p. 145°–148° C. (0.05 mm Hg).

Method B

Another procedure involved heating the alcohol and tBAA, (or beta-ketoester) in solvent, in a round-bottom flask with magnetic stirrer, 5-plate Oldershaw column and still head for removal of the t-butanol co-product. For example: a solution of n-octanol (13 g, 0.1 mol), tBAA (16.6 g, 0.105 mol) and 50 mL toluene was heated at reflux until the theoretical amount of t-butyl alcohol was obtained (ca. 15 min. after reflux). The reaction mixture was subsequently concentrated and distilled to give 17.8 g (83.2%) octyl acetoacetate b.p. 95°–110° C. (1.0 mm Hg).

Method C

This method is a modification of Method B. In a 300 mL, 3-neck flask with magnetic stirrer, 5-plate Oldershaw column with still head and thermometers in the base and head of the system, was placed 33.52 g tBAA, 30.1 g phenol, 110 mL xylene and 100 mL cyclohexane. The solution was heated to reflux and the t-BuOH/cyclohexane azeotrope removed by distillation. Additional cyclohexane can be added to the reaction if necessary. Total yield of phenyl acetoacetate from this process was 21.9 g (74%).

Examples of acetoacetylated materials prepared by methods A-C are given in Table 1. Examples of other beta-ketoesters prepared, by method B are given in Table 2.

TABLE 1

Yield of Various Acetoacetylated Materials Using t-Butyl Acetoacetate (tBAA)

| Nucleophile[b], grams | | g(tBAA) | mL Solvent | Yield (%) | Experimental[a] Method |
|---|---|---|---|---|---|
| TMP | 47.5 | 171.00 | 100 | 90[d] | B |
| TMPD | 10.1 | 22.4 | 30 | 87[c] | A |
| NPG | 10.0 | 32.1 | 32 | 87[c] | A |
| NPG | 159.2 | 491.3 | 450 | 81[c] | B |
| HEMA[g] | 16.8 | 20.5 | 65 | 70 | B |
| CHDM | 9.8 | 22.1 | 28 | 69[c,e] | A |
| HNBu$_2$ | 7.65 | 9.24 | 25 | 96 | A |
| PhOH | . | . | . | 34 | A |
|  | 30.1 | 33.5 | 110/100[f] | 74 | C |
| Ph-NH$_2$ | 10.0 | 17.2 | 25 | 83 | A |
| nBuOH | 10.0 | 21.4 | 40 | 87 | A |
| n-OctOH | 13.0 | 16.6 | 50 | 83 | B |
| Ph-CH$_2$OH | 10.8 | 16.6 | 50 | 89 | B |
| Ester diol 204 | 10.2 | 16.2 | 60 | 88[c] | B |
| p(NO$_2$)PhNH$_2$ | 13.8 | 16.2 | 50 | 86 | B |
| 1-Me-Cyclohexan-1-ol | 11.4 | 16.2 | 50 | 83 | B |
| 3-Me-2-buten-1-ol | 8.6 | 16.2 | 50 | 97 | B |

[a]Refers to the description of the experimental method set forth in Example 1.
[b]Abbreviations used:
TMPD = 2,2,4-trimethyl-1,3-pentanediol
TMP = trimethylolpropane
NPG = neopentyl glycol or 2,2-dimethyl-1,3-propanediol
HEMA = hydroxyethyl methacrylate
CHDM = cyclohexane-1,4-dimethanol
HNBu$_2$ = dibutyl amine
Ester diol 204 (sold by Union Carbide). Also known as HPHP—hydroxy pivaloyl hydroxy pivaloate
[c]Yield of bis-acetoacetate for TMPD, NPG, CHDM and Ester diol 204.
[d]Yield of tris-acetoacetate for TMP.
[e]Yield of crystalline material, some cis isomer lost in recrystallization.
[f]110 mL xylene, 100 mL cyclohexane.
[g]Reaction also contained 67 mg benzoquinone and 137 mg BHT.

TABLE 2

Yield for Reaction of $$R'-\underset{\underset{R'''}{|}}{\overset{\overset{O}{\|}}{C}}-C-\overset{\overset{O}{\|}}{C}-O-C\begin{smallmatrix}\diagup C(1)R''_3 \\ -C(2)R''_3 \\ \diagdown C(3)R''_3\end{smallmatrix}$$

With Various Nucleophiles by Method B

| | R'' | | | | | g | mL | |
| Nuc (g) | C(1) | C(2) | C(3) | R''' | R' | (ketoester) | (solvent) | Yield |
|---|---|---|---|---|---|---|---|---|
| p-NO$_2$PhNH$_2$ (8.3) | H$_3$ | H$_3$ | H, H, CH$_3$ | H | CH$_3$ | 10.7 | 60 | 91% |
| Ph—CH$_2$OH (10.8) | H$_3$ | H$_3$ | H, H, CH$_3$ | H | CH$_3$ | 13.3 | 60 | 68% |
| PhCH$_2$OH (4.8) | H$_3$ | H$_3$ | H$_3$ | Cl | CH$_3$ | 2.7 | 50 | 81% |
| OctOH (3.3) | H$_3$ | H$_3$ | H$_3$ | Cl | CH$_3$ | 5.5 | 50 | 98% |
| OctOH (7.0) | H$_3$ | H$_3$ | H$_3$ | CH$_3$ | CH$_3$ | 3.3 | 60 | 88% |
| nBuOH (0.85) | H$_3$ | H$_3$ | H$_3$ | H | C(CH$_3$)$_3$ | 0.93 | 10 | 91% |

TABLE 2-continued

Yield for Reaction of

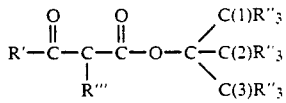

With Various Nucleophiles by Method B

| | R'' | | | | | g | mL | |
|---|---|---|---|---|---|---|---|---|
| Nuc (g) | C(1) | C(2) | C(3) | R''' | R' | (ketoester) | (solvent) | Yield |
| 2-Cl-4-(NO$_2$)—PhNH$_2$ (1.36) | H$_3$ | H$_3$ | H$_3$ | H | C(CH$_3$)$_3$ | 1.32 | 20 | 95% |
| n-OctOH (0.937) | H$_3$ | H$_3$ | H$_3$ | H | CH$_2$Cl | 1.11 | 10 | 54% |

The results presented in Tables 1 and 2 demonstrate the generality of the invention process for the preparation of a wide variety of low molecular weight acetoacetated materials. The generality of the invention process for polymeric nucleophiles is demonstrated in Examples 3 and 4.

EXAMPLE 2

The following procedure was used to determine the relative rates of reaction of various nucleophiles with the beta-ketoesters. A solution of 4.7–5.4 mmol acetoacetate (ketoester), nucleophile (4.9–50 mmol) and p-dichlorobenzene internal standard (450–500 mg) diluted to 10 mL with p-xylene was placed in a flask with condenser and N$_2$ inlet. The apparatus was placed in a constant temperature bath, samples periodically withdrawn and the extent of reaction assessed by gas chromatography. Rate data obtained by this method are given in Tables 3 and 4. In addition, the advantages of the invention process for the reaction of t-butyl pivaloyl acetate with 2-chloro-4-nitroaniline are shown in Table 5.

TABLE 3

Rate Constants for Reactions of QOAcAc
With n-BuOH at 91.85° C.

| Q | k × 10$^{4a}$ | [nBuOH]$^b$ | [QOAcAc]$^c$ |
|---|---|---|---|
| tBu | 1.716 | 0.492 | 0.474 |
| tBu | 1.662 | 2.623 | 0.475 |
| tBu$^d$ | 1.859 | 1.027 | 0.472 |
| tBu | 1.559 | 0.174 | 0.068 |
| Et | 0.102 | 0.526 | 0.473 |
| Et | 0.136 | 4.987 | 0.477 |
| Me | 0.097 | 0.611 | 0.551 |
| iBu | 0.138 | 1.068 | 0.474 |
| iPr | 0.140 | 1.070 | 0.537 |
| HC(iPr)$_2$ | 0.083 | 1.046 | 0.477 |
| tAm | 1.460 | 1.072 | 0.495 |

TABLE 3-continued

Rate Constants for Reactions of QOAcAc
With n-BuOH at 91.85° C.

| Q | k × 10$^{4a}$ | [nBuOH]$^b$ | [QOAcAc]$^c$ |
|---|---|---|---|
| TKD | 1.07 | | |

$^a$First-order rate constant in sec$^{-1}$.
$^b$Molar concentration of n-BuOH.
$^c$Molar concentration of acetoacetate.
$^d$Acetoacetate distilled prior to use.

TABLE 4

First-Order Rate Constants (In Sec$^{-1}$) For Reaction
of Various Beta-Ketoesters With Nucleophiles

| Acetoacetate | [AcAc] | [n-OctOH] | k$_1$ × 10$^6$ |
|---|---|---|---|
| A. Rate of Reaction of 2-Chloro Acetoacetates with n-Octanol at 114.9° C. | | | |
| t-Butyl | 0.48 | 0.72 | 8.55 |
| t-Butyl | 0.48 | 2.88 | 8.62 |
| Ethyl | 0.48 | 2.88 | 2.93 |
| B. Rate of Reaction of 2-Methyl Acetoacetates with n-Octanol at 114.9° C. | | | |
| t-Butyl | 0.48 | 0.72 | 24.3 |
| t-Butyl | 0.48 | 2.88 | 29.7 |
| Ethyl | 0.48 | 2.88 | 3.7 |

| Acetoacetate | [AcAc] | [n-OctOH] | k$_1$ × 10$^4$ |
|---|---|---|---|
| C. Rate of Reaction of 4-Chloro Acetoacetates with n-Octanol at 91.9° C. | | | |
| t-Butyl | 0.48 | 2.88 | 3.00 |
| t-Butyl | 0.48 | 0.72 | 2.78 |
| Ethyl | 0.48 | 0.72 | 0.21 |
| Ethyl | 0.48 | 2.88 | 0.27 |

| Ester | | | k$_1$ × 10$^4$ |
|---|---|---|---|
| D. Rate of Reaction of Pivaloyl Acetates with n-BuOH at 91.9° C. | | | |
| t-Bu | | | 1.54 |
| Me | | | 0.13 |

TABLE 5

Percent Conversion to Cl-Nitro-Anilide with
Methyl and t-Butyl Pivaloyl Acetates

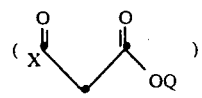

| | % Conversion | |
|---|---|---|
| Time (min) | Q = Me | Q = tBu |
| 90 | 4.2 | 26.0 |
| 230 | 10.0 | 36.0 |
| 480 | 14.0 | 45.5 |
| 1400 | 24.0 | 60.0 |

The rate data presented in Tables 3 and 4 demonstrate the advantage of the invention process relative to prior art processes employing methyl or ethyl acetoacetate. Rate enhancements of an order of magnitude and higher are routinely observed for the invention process relative to prior art processes.

The percent conversion results summarized in Table 5 demonstrate that t-butyl pivaloyl acetate gives much higher yields of desired product than does methyl pivaloyl acetate. At all time points analyzed, the yield of product formed from t-butyl pivaloyl acetate is more than double the yield of product obtained from methyl pivaloyl acetate.

EXAMPLE 3—Acetoacetylation of Polyester Resins

Run No. 1

To a solution of 450.3 g of polyester resin comprised of 44.2% neopentyl glycol (NPG), 3.0% trimethylolpropane (TMP), 28.9% dimethylcyclohexane dicarboxylate (DMCD), 23.9% isophthalic acid with molecular weight of 858.1297 and a hydroxyl number of about 210 in xylene solvent (85% solids) at 140° C. was added 120.0 g tBAA. The t-butyl alcohol begin to distill from the reaction immediately and the process was complete in 2 hours. When an identical polyester solution was treated with either ethyl or methyl acetoacetate, the rate of acetoacetylation (as noted by the evolution of alcohol) was 2-6 hours slower, even f 0.1 wt % of a dibutyltin oxide catalyst was used. Analysis of the resultant polyesters by proton nuclear magnetic resonance spectroscopy ($^1$H-NMR) showed that the polyesters acetoacetylated with methyl acetoacetate (MAA) or ethyl acetoacetate (EAA) and catalyst had been reduced in molecular weight, while no such polyester breakdown was noted for the reaction with tBAA.

Run No. 2

In another experiment 102.35 g of a high-solids polyester coating resin comprised of 2,2,4-trimethyl-1,3-propanediol (TMPD; 54 wt %), TMP (4.7%), isophthalic acid (22%) and adipic acid (19.3%) with a hydroxyl number of about 170 and molecular weight 900-1100 was placed in 500 mL 3-neck flask with addition funnel, 5-plate Oldershaw column with still head and thermometers in the base and head. The resin was diluted to 69% solids with xylene, heated to 120° C., 25.15 g of tBAA were added and the resultant t-butanol was removed by distillation over a 2 hr. period to obtain an acetoacetylated resin in which 50% of the hydroxyl end groups were acetoacetylated. The ratio of tBAA to polyester could be altered to produce material with 11%, 18%, 25% or 85% acetoacetylation.

Run No. 3

In another experiment 392.8 g of a high-solids coating resin comprised of 35.3 wt % isophthalic acid and 64.7 wt % TMPD with a hydroxyl number of about 285-265 and molecular weight 600-800 was placed in a 3-neck flask with addition funnel, mechanical stirrer, steam-heated reflux column topped with a Dean-Stark trap with condenser. The neat resin was heated to 150° C. and 272.1 g tBAA was added drop-wise over a period of 1.5 hr. Two hours after the addition was begun 94% of the theoretical amount of t-butyl alcohol was obtained. Analysis of the resulting resin by $^1$H-NMR spectroscopy again indicated the production of an acetoacetylated resin with 89% of the hydroxyls acetoacetylated.

Run No. 4

In a 250 mL round bottom flask with 6" Vigreaux column, still head, magnetic stirrer and $N_2$ inlet was placed 25.48 g of a polyester comprised of NPG and terephthalic acid with a hydroxyl number of about 45 and number average molecular weight of about 3089, 1.92 g tBAA and 35 mL n-butyl acetate. The solution was warmed to reflux and solvent removed until the head temperature reached 110° C. (approximately 45 minutes). NMR spectroscopic analysis of the resulting concentrated solution showed that approximately 60% of the end groups had been acetoacetylated.

The above runs demonstrate that the invention process can be used for the acetoacetylation of a variety of hydroxylated polyester resins. The degree of acetoacetylation is readily controlled by varying the t-butyl acetoacetate/polyester ratio.

EXAMPLE 4—Acetoacetylation of Acrylic Resins

Run No. 1

In a 2L 3-neck flask with magnetic stirrer, 5-plate Oldershaw column with still head and nitrogen inlet was placed 517.4 g of an acrylic polymer with acid number 10.6, and hydroxyl number of about 169, in butyl acetate as a 61.3% solid solution. A 112.8 g sample of tBAA was placed in the flask and the solution was heated to reflux with removal of t-butanol over a period of 50 min. The resulting acetoacetylated polymer was identical by NMR spectroscopy with one prepared by reaction of the polymer with diketene (ca. 50% acetoacetylation). An identical material was also obtained if the reaction was carried out on the polymer in methyl isobutyl ketone solvent.

Run No. 2

In another experiment 157 g of a 60% solids solution in ethoxyethylpropionate (EEP) of an acrylic terpolymer prepared from 48 wt % of methylmethacrylate, 29 wt % butyl methacrylate and 22 wt % hydroxyethyl methacrylate was acetoacetylated with 12.8 g t-butyl acetoacetate (tBAA) by heating the solution to 160° C. and removing the resulting t-butanol by distillation through a 5-plate Oldershaw column. This produced a material in which approximately 50% of the available hydroxyls had been acetoacetylated. This same resin was acetoacetylated so as to acetoacetylate about 85% of the available hydroxyls by using 188 g of the resin solution and 26.0 g tBAA.

Run No. 3

Using the same method as described in Run No. 2, 155 g of a 60% solids solution in EEP of an acrylic copolymer prepared from 70 mol % methyl methacrylate and 30 mol % hydroxyethyl methacrylate was acetoacetylated with 21.76 g tBAA to produce a polymer in which approximately 50% of the hydroxyls had been acetoacetylated. This same polymer was acetoacetylated so as to acetoacetylate about 85% of the hydroxyls by treating 166.7 g of the resin solution with 36.9 g tBAA.

The above runs demonstrate that the invention process can be used for the acetoacetylation of hydroxylated acrylic resins. As was the case with hydroxylated polyesters as reactive nucleophiles, it is possible to control the degree of acetoacetylation by varying the t-butyl acetoacetate/acrylic resin ratio.

The invention has been described in detail with particular reference to preferred embodiments thereof, but it will be understood that variations and modifications can be effected within the spirit and scope of the invention.

We claim:

1. Method for the functionalization of nucleophiles having the structural formula:

$$HY—R_x$$

wherein

Y is selected from the group consisting of nitrogen, oxygen and sulfur;

R is selected from the group consisting of $C_1$ to $C_{12}$ hydrocarbyl radicals substituted with 0 to 3 hydroxyl units, formyl, nitro, chlorine atoms, bromine atoms, ester moieties of the structure:

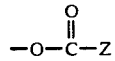

wherein Z is a hydrocarbyl moiety having 1 to 6 carbon atoms, and alkoxy moieties of the structure, —OZ, wherein Z is as defined above; and wherein R can also be H when Y is N; and x is 1 when Y is O or S, and x is 2 when Y is N; said process comprising contacting said nucleophile with a compound having the structure

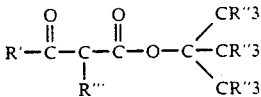

wherein

R' is a $C_1$ to $C_8$ alkyl, aryl or halide substituted alkyl or aryl moiety, each R'' is independently selected from H, a $C_1$ to $C_8$ alkyl moiety, or a halogen, and R''' is selected from H, $C_1$ to $C_4$ alkyl moieties, $C_4$ to $C_{10}$ aromatic, heteroaromatic and substituted aromatic moieties, or halogens; wherein said contacting is carried out in the essential absence of a tetraalkyl titanate and at a temperature and for a time sufficient to produce the desired produce wherein at least one hydroxy, mercapto, amino or

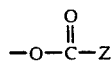

moiety of said nucleophile has been transacylated by the acyl moiety

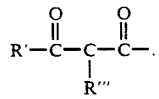

2. A method in accordance with claim 1 wherein said nucleophile is selected from the group consisting of polyols having the structure:

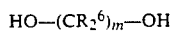

wherein each $R^6$ is independently selected from the group consisting of H, OH, and $C_1$ to $C_4$ alkyl radicals, and m can vary from 2 up to about 12.

* * * * *